(12) United States Patent
Lee et al.

(10) Patent No.: US 9,322,004 B2
(45) Date of Patent: Apr. 26, 2016

(54) METHOD OF PRODUCING FATTY ACID ALKYL ESTER USING MICROORGANISMS HAVING ABILITY TO PRODUCE OIL

(75) Inventors: Sang Yup Lee, Daejeon (KR); Yong Jun Choi, Daejeon (KR)

(73) Assignee: KOREA ADVANCED INSTITUTE OF SCIENCE AND TECHNOLOGY, Daejeon (KR)

(*) Notice: Subject to any disclaimer, the term of this patent is extended or adjusted under 35 U.S.C. 154(b) by 732 days.

(21) Appl. No.: 13/384,576

(22) PCT Filed: Jul. 19, 2010

(86) PCT No.: PCT/KR2010/004701
§ 371 (c)(1),
(2), (4) Date: Apr. 10, 2012

(87) PCT Pub. No.: WO2011/008058
PCT Pub. Date: Jan. 20, 2011

(65) Prior Publication Data
US 2012/0190088 A1    Jul. 26, 2012

(30) Foreign Application Priority Data
Jul. 17, 2009   (KR) .......................... 10-2009-0065490

(51) Int. Cl.
*C12P 7/64*     (2006.01)
*C12N 9/20*     (2006.01)

(52) U.S. Cl.
CPC . *C12N 9/20* (2013.01); *C12P 7/649* (2013.01); *C12Y 301/01003* (2013.01); *Y02E 50/13* (2013.01); *Y02P 20/52* (2015.11)

(58) Field of Classification Search
CPC ........ C12P 7/6409; C12P 7/6418; C12P 7/64; C12P 7/649; C12P 7/6436
See application file for complete search history.

(56) References Cited

U.S. PATENT DOCUMENTS 4,164,506 A     8/1979   Kawahara et al.
5,942,659 A *   8/1999   Alibert et al. ................. 800/281
(Continued)

FOREIGN PATENT DOCUMENTS

EP    127104 A1   12/1984
EP    184740 A2   11/1985
(Continued)

OTHER PUBLICATIONS

GenBank Accession No. NC_008596 REGION: 246357..247199 (Apr. 2009).*
(Continued)

*Primary Examiner* — Rebecca Prouty
(74) *Attorney, Agent, or Firm* — Knobbe, Martens, Olson & Bear, LLP

(57) ABSTRACT

The present invention relates to a method of producing a fatty acid alkyl ester using microorganisms having the ability to produce oil, and more particularly to a method of producing a fatty acid alkyl ester, the method comprising culturing microorganisms having the ability to produce oil, thus accumulating a large amount of oil in the microorganisms, inducing the autolysis of the produced oil in the microorganisms to produce a free fatty acid, and converting the free fatty acid into an alkyl ester. According to the method of the present invention, oil accumulated in microorganisms, such as triacylglycerol that is typical oil produced by microorganisms, can be converted into a fatty acid alkyl ester with high efficiency using a metabolic engineering approach. Thus, the method of the present invention is useful for the industrial production of a fatty acid alkyl ester which has been recently found to be effective as biodiesel.

5 Claims, 7 Drawing Sheets

| Strains | FAME concentration produced from free fatty acids in culture media(g/l) | | | | | | | | |
|---|---|---|---|---|---|---|---|---|---|
| | 13:0 | 14:0 | 15:0 | 16:0 | 17:0 | 18:0 | 20:0 | 22:0 | Total(g/L) |
| Rhodococcus opacus strain PD630 | - | - | - | - | 0.171 | - | - | - | 0.171 |
| R.opacus _rpROUC18KM_Ara | - | 0.153 | - | 0.214 | - | - | - | - | 0.367 |
| R.opacus _rpROUC18_Af7G | - | - | - | 0.066 | 0.053 | - | - | - | 0.119 |
| R.opacus _rpROUC18_PAO | - | - | 0.173 | - | - | - | 0.052 | - | 0.225 |
| R.opacus _rpROUC18KM_MAG | - | - | - | - | - | - | 0.210 | - | 0.210 |
| R.opacus -rpROUC18KM_Ara_MAG | 0.204 | 0.327 | - | - | - | - | - | - | 0.525 |
| R.opacus_rpROUC18_Af7G_MAG | - | 0.236 | - | 0.195 | - | - | - | - | 0.431 |
| R.opacus_rpROUC18_PAO_MAG | - | 0.098 | 0.081 | 0.126 | 0.055 | 0.180 | - | - | 0.539 |

(56) References Cited

U.S. PATENT DOCUMENTS

| | | |
|---|---|---|
| 2005/0011112 A1 | 1/2005 | Khalil |
| 2008/0038804 A1 | 2/2008 | Du |
| 2008/0229454 A1 | 9/2008 | Napier |
| 2009/0030219 A1 | 1/2009 | Su |

FOREIGN PATENT DOCUMENTS

| | | | |
|---|---|---|---|
| EP | 708813 A | | 5/1996 |
| EP | 1790731 A2 | | 5/2007 |
| WO | WO9502661 | | 1/1995 |
| WO | 2008009772 A1 | | 1/2008 |
| WO | 2009/035551 | * | 3/2009 |

OTHER PUBLICATIONS

M. Waltermann et al. "Rhodococcus opacus Strain PD630 as a New Source of High-value Single-cell Oil? Isolation and Characterization of Triacylglycerols and Other Storage Lipids", Microbiology 146:1143-1149 (2000).*

Lee et al., "Batch and continuous cultures of Mannheimia succiniciproducens MBEL55E for the production of succinic acid from whey and corn steep liquor" Bioprocess Biosyst. Eng., 26: 63, 2003.

Lee et al., "Isolation and characterization of a new succinic acid-producing bacterium, Mannheimia succiniciproducens MBEL55E, from bovine rumen" Appl. Microbiol. Biotechnol., 58: 663, 2002.

Lee et al., "Biological conversion of wood hydrolysate to succinic acid by Anaerobiospirillum succiniciproducens" Biotechnol. Lett., 25: 111, 2003.

Lee et al., "Batch and continuous cultivation of Anaerobiospirillum succiniciproducens for the production of succinic acid from whey" Appl. Microbiol. Biotechnol., 54: 23, 2000.

Lee et al., "Succinic Acid Production with Reduced By-Product Formation in the Fermentation of Anaerobiospirillum succiniciproducens Using Glycerol as a Carbon Source" Biotechnol. Bioeng., 72: 41, 2001.

* cited by examiner

FIG. 4

| Strain or plasmid | Relevant characteristic(s) |
|---|---|
| R.opacus strain PD630 | |
| rpROUC18 | Ap$^r$; Rhococcus rhodochrous origin; Mycobacterium smegmatis acetamide inducible promoter |
| rpROUC18KM | Ap$^r$; Km resist marker from pTak15k plasmid; Rhococcus rhodochrous origin; Mycobacterium smegmatis acetamide inducible promoter; AatII |
| rpROUC18KM_Ara | Ap$^r$; Arabidopsis thaliana TAG lipase; NcoI, PstI |
| rpROUC18_Af7G | Ap$^r$; Aspergillus fumigates TAG 7G lipase; AatII, XmaI |
| rpROUC18_PAO | Ap$^r$; Pseudomonas aeruginosa TAG lipase; AatII, HindIII |
| rpROUC18KM_MAG | Ap$^r$; M. smegmatis MAG lipase; NarI, PstI |
| rpROUC18KM_Ara_MAG | Ap$^r$; A. thaliana TAG lipase; NcoI, PstI; M. smegmatis MAG lipase, NarI, PstI |
| rpROUC18_Af7G_MAG | Ap$^r$; A. fumigates TAG 7G lipase; AatII, XmaI; M. smegmatis MAG lipase; overlapping PCR; SacI |
| rpROUC18_PAO_MAG | Ap$^r$; P. aeruginosa TAG lipase; AatII, HindIII; M. smegmatis MAG lipase; SacI |

FIG. 5

| Strains | Free fatty acids concentration in culture media (g/l) | | | | | | | | | |
|---|---|---|---|---|---|---|---|---|---|---|
| | 13:0 | 14:0 | 15:0 | 16:0 | 17:0 | 18:0 | 20:0 | 22:0 | Total(g/L) |
| Rhodococcus opacus strain PD630 | - | - | 0.0688 | - | 0.0109 | 0.0537 | - | 0.2234 | 0.3569 |
| R. opacus_rpROUC18KM_Ara | - | 0.138 | - | - | - | 0.6749 | 0.0331 | - | 0.708 |
| R. opacus_rpROUC18_AtTG | - | - | - | 0.114 | - | 0.335 | - | - | 0.587 |
| R. opacus_rpROUC18_PAO | - | - | 0.347 | - | - | 0.3324 | - | - | 0.680 |
| R. opacus_rpROUC18KM_MAG | - | - | 0.219 | - | - | 0.353 | 0.156 | - | 0.509 |
| R. opacus_rpROUC18KM_Ara_MAG | - | - | 0.297 | - | - | 0.738 | 0.160 | - | 1.116 |
| R. opacus_rpROUC18_AtTG_MAG | - | - | - | - | - | 0.669 | - | - | 0.966 |
| R. opacus_rpROUC18_PAO_MAG | - | - | - | 0.676 | 0.423 | - | - | - | 1.099 |

FIG. 7

| Strains | FAME concentration produced from free fatty acids in culture media (g/l) | | | | | | | | | |
|---|---|---|---|---|---|---|---|---|---|---|
| | 13:0 | 14:0 | 15:0 | 16:0 | 17:0 | 18:0 | 20:0 | 22:0 | Total (g/L) |
| Rhodococcus opacus strain PD630 | - | - | - | - | 0.171 | - | - | - | 0.171 |
| R.opacus _rpROUC18KM _Ara | - | 0.153 | - | 0.214 | - | - | - | - | 0.367 |
| R.opacus _rpROUC18 _Af7G | - | - | - | 0.066 | 0.053 | - | - | - | 0.119 |
| R.opacus _rpROUC18 _PAO | - | - | 0.173 | - | - | - | 0.052 | - | 0.225 |
| R.opacus _rpROUC18KM _MAG | - | 0.327 | - | - | - | - | 0.210 | - | 0.210 |
| R.opacus -rpROUC18KM _Ara_MAG | 0.204 | 0.236 | - | 0.195 | - | - | - | - | 0.525 |
| R.opacus _rpROUC18 _Af7G_MAG | - | 0.098 | 0.081 | 0.126 | 0.055 | 0.180 | - | - | 0.431 |
| R.opacus _rpROUC18 _PAO_MAG | - | - | - | - | - | - | - | - | 0.539 | ical engineering method, and then inducing the autoly-
METHOD OF PRODUCING FATTY ACID ALKYL ESTER USING MICROORGANISMS HAVING ABILITY TO PRODUCE OIL

TECHNICAL FIELD

The present invention relates to a method of producing a fatty acid alkyl ester using microorganisms having the ability to produce oil, and more particularly to a method of producing a fatty acid alkyl ester, the method comprising culturing microorganisms having the ability to produce oil, thus accumulating a large amount of oil in the microorganisms, inducing the autolysis of the produced oil in the microorganisms to produce a free fatty acid, and converting the free fatty acid into an alkyl ester.

BACKGROUND ART

Recently, due to high oil prices and environmental concerns, the microbial production of biofuels has received a great deal of attention. Also, biodiesel has been substituted for light oil or a mixture of biodiesel with light oil has emerged as an alternative fuel that can be used in diesel engines, and thus the market size of biodiesel has rapidly increased. In the European Union (EU) in 2008, 6.6 million tons of biodiesel was produced, which a market size of 5.5 billion euro (Biodiesel Market, Frost & Sullivan). Also, in USA in 2006, 3 billion gallons of biodiesel was produced (Biodiesel Market, Global Industry Analysts Inc, 2006. 5).

Biodiesel is advantageous in that it has a high burning rate and thus low emission of poisonous gases, an about 10% lower heating value than that of light oil, and a higher ignition point than that of light oil, indicating that it is more stable during storage and transport. Biodiesel has been mainly produced by processing the fatty components of animals and plant so as to have properties similar to those of light oils or allowing vegetable oils and fats (rice bran, waste cooking oil, soybean oil, rapeseed oil, etc.) to react with alcohol. However, in this case, there is a shortcoming in that it is difficult to produce biodiesel in large amounts. Thus, if biodiesel suitable as an alternative fuel for light oil is produced in large amounts using microorganisms, the import of crude oil will decrease and the emission of greenhouse gases will decrease, resulting in environmental effects.

Meanwhile, oil is an energy carrier that is synthesized and accumulated in microbial cells when microorganisms are rich in carbon sources but lack other growth factors (nitrogen, phosphorus, oxygen, sulfur, etc.). When the environment of microbial growth changes so that the other growth factors are supplied to microorganisms, the accumulated oil will be degraded and used as an energy source. It is known that oil can consist of more than 100 kinds of monomers depending on the kind of oil-producing microorganism, the kind of chemical material supplied, changes in culture conditions, etc.

Recently, the technology of producing fatty acid alkyl ester by adding alcohol to vegetable fatty acid such as a sugar cane was developed, and the produced fatty acid alkyl ester is currently being used as a biodiesel fuel. Also, methods for esterifying free fatty acids are disclosed in European Patent Publication No. 127104A, European Patent Publication No. 184740A and U.S. Pat. No. 4,164,506. According to the disclosures of these patents, an esterification reaction is carried out by heating a mixture of fatty acid and fatty acid triglyceride together with methanol. In addition, European Patent Publication No. 708813A discloses a method of producing fatty acid alkyl ester from oils and fats in an increased yield, in which free fatty acid is separated from a glycerin resulting from ester interchange and is then esterified.

However, in this method, it is difficult to obtain large amounts of fatty acid or free fatty acid. In addition, it is difficult to increase the accumulation and production of vegetable fatty acids that are currently most frequently used, because the growth period of plants is long and a metabolic engineering approach to produce the vegetable fatty acids is somewhat difficult.

Accordingly, the present inventors have made extensive efforts to develop a novel method capable of producing a fatty acid alkyl ester, which can be used as biodiesel, with high efficiency and productivity using a metabolic engineering approach, and as a result, have found that the fatty acid alkyl ester can be produced with high efficiency by maximizing the production of oil in oil-producing microorganisms using a metabolic engineering method, and then inducing the autolysis of the oil in the microorganisms to produce a free fatty acid which is then converted to an alkyl ester, thereby completing the present invention.

DISCLOSURE OF INVENTION

It is an object of the present invention to provide a novel method capable of producing large amounts of a fatty acid alkyl ester, which can be used as biodiesel, with high efficiency and productivity using a metabolic engineering approach.

To achieve the above object, the present invention provides a method of producing a fatty acid alkyl ester, the method comprising the steps of:
(a) culturing microorganisms having the ability to produce oil, thus producing oil;
(b) inducing the autolysis of the produced oil in the microorganisms to produce a free fatty acid; and
(c) adding an alcohol to the produced free fatty acid and reacting the alcohol with the free fatty acid to produce a fatty acid alkyl ester.

The present invention also provides a method of producing a fatty acid methyl ester using microorganisms having the ability to produce oil and containing a gene encoding lipase, the method comprising the steps of:
(a) culturing microorganisms having the ability to produce oil and containing a gene encoding lipase, thus producing oil;
(b) inducing the autolysis of the produced oil by lipase in the microorganisms to produce a free fatty acid; and
(c) adding methanol to the produced free fatty acid and reacting the methanol with the free fatty acid to produce a fatty acid methyl ester.

Other features and embodiments of the present invention will be more apparent from the following detailed descriptions and the appended claims

BRIEF DESCRIPTION OF THE DRAWINGS

FIG. 4 shows the types and information of plasmids made based on the information shown in Table 1.

FIG. 5 shows the results of gas chromatography analysis of free fatty acids.

FIGS. 6 and 7 show the results of gas chromatography analysis of fatty acid methyl ester.

BEST MODE FOR CARRYING OUT THE INVENTION

Figure 1:
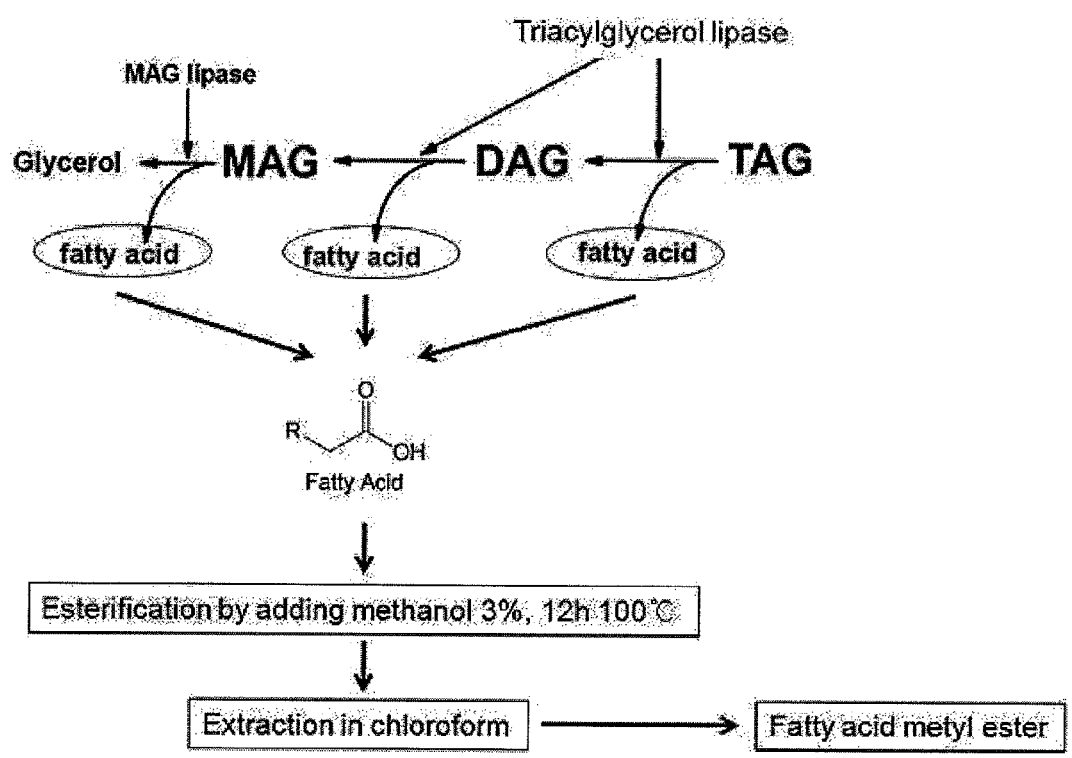
FIG. 1 shows a process of producing a fatty acid methyl ester with high efficiency from the typical oil triacylglycerol (TAG) using *Rhodococcus opacus* PD630.

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

The definition of main terms used in the detailed description of the invention is as follows.

As used herein, the term "oil" refers to an energy carrier that is synthesized and accumulated in the cells of microorganisms when the microorganisms are rich in carbon sources but lack other growth factors (nitrogen, phosphorus, oxygen, sulfur, etc.). It is a free fatty acid precursor that is hydrolyzed into free fatty acids and glycerol.

As used herein, the term "fatty acids" refers to chain type of saturated or unsaturated monocarboxylic acids. These fatty acids are classified according to carbon chain length and saturation, and fatty acids resulting from the hydrolysis of oil (i.e., fat) are referred to as "free fatty acids".

In one aspect, the present invention is directed to a method of producing a fatty acid alkyl ester using microorganisms having the ability to produce oil, and more particularly to a method of producing a fatty acid alkyl ester, the method comprising the steps of:

(a) culturing microorganisms having the ability to produce oil, thus producing oil;

(b) inducing the autolysis of the produced oil in the microorganisms to produce a free fatty acid; and (c) adding an alcohol to the produced free fatty acid and reacting the alcohol with the free fatty acid to produce a fatty acid alkyl ester.

In the present invention, the oil may be any oil produced in microorganisms, and examples thereof include, but are not limited to, triacylglycerol (TAG), diacylglycerol (DAG), monoacylglycerol (MAG), phospholipid, sterol lipid, sphingolipid, saccharolipid, prenol lipid, and polyketide.

Herein, the free fatty acid that is produced by the decomposition of the oil may be a saturated or unsaturated fatty acid, in which the unsaturated fatty acid refers to a fatty acid having one or more double bonds in the carbon chain, and examples thereof include oleic acid, linoleic acid, linolenic acid, palmitoleic acid, ricinoleic acid, vaccenic acid, gadoleic acid, arachidonic acid, EPA (5,8,11,14,17-eicosapentaenoic acid), erucic acid, DHA (4,7,10,13,16,19-docosahexaenoic acid), etc. In addition, the saturated fatty acid refers to a fatty acid having no double bond in the carbon chain, and examples thereof include butyric acid, caproic acid, caprylic acid, capric acid, lauric acid, myristic acid, palmitic acid, stearic acid, arachidic acid, behenic acid, lignoceric acid, etc. The fatty acid that is used in the present invention may be substituted with substituent selected from the group consisting of, but not limited to, an aromatic ring group, an epoxy group, a cyano group and a halogen group.

In the present invention, the oil that is a free fatty acid precursor is produced by microorganisms having the ability to produce oil. Examples of the microorganisms having the ability to produce oil include *Aeromonas* sp., *Achromobacter* sp., *Acidovorax delafieldii*, *Acidovax facilis*, *Acinetobacter* sp., *Actinomyces* sp., *Aeromonas Alcaligenes* sp., *Alteromonas* sp., *Althornia* sp., *Aplanochytrium* sp., *Aspergillus* sp., *Amoebobacter* sp., *Aphanocapsa* sp., *Aphanothece* sp. *Aquaspirillum autotrophicum*, *Azorhizobium caulinodans*, *Azospirillum* sp., *Azospirillum* sp., *Azotobacter* sp., *Bacillus* sp., *Beggiatoa* sp., *Beijerinckia* sp., *Beneckea* sp., *Blakeslea* sp., *Bordetella pertussis*, *Bradyrhizobium japonicum*, *Caryophanon latum*, *Caulobacter* sp., *Chlorogloea* sp., *Chromatium* sp., *Chromobacterium* sp., *Clostridium* sp., *Comamonas* sp., *Corynebacterium* sp., *Crypthecodinium* sp., *Cyanobacteria* sp., *Derxia* sp., *Desulfonema* sp., *Desulfosarcina variabilis*, *Desulfovibrio sapovorans*, *Ectothiorhodospira* sp., *Elina* sp., *Entomophthora* sp., *Ferrobacillus ferroxidans*, *Flavobacterium* sp., *Haemophilus influenzae*, *Halobacterium* sp., *Haloferax mediterranei*, *Hydroclathratus clathratus*, *Hydrogenomonas facilis*, *Hydrogenophaga* sp., *Hyphomicrobium* sp., *Ilyobacter delafieldii*, *Japonochytrium* sp., *Labrys monachus*, *Lamprocystis roseopersicina*, *Lampropedia hyalina*, *Legionella* sp., *Leptothrix discophorus*, *Methylobacterium* sp., *Methylosinus* sp., *Micrococcus* sp., *Mortierella* sp., *Mycobacterium* sp., *Nitrobacter* sp., *Nocardia* sp., *Paracoccus dentrificans*, *Oscillatoria limosa*, *Penicillium cyclopium*, *Photobacterium* sp., *Physarum ploycephalum*, *Phycomyces* sp., *Pseudomonas* sp., *Pythium* sp., *Ralstonia* sp., *Rhizobium* sp., *Rhodobacillus* sp., *Rhodobacter* sp., *Rhodococcus* sp., *Rhodocyclus* sp., *Rhodomicrobium vannielii*, *Rhodopseudomonas* sp., *Rhodospirillum* sp., *Schizochytrium* sp., *Sphingomonas paucimobilis*, *Spirillum* sp., *Spirulina* sp., *Staphylococcus* sp., *Stella* sp., *Streptomyces* sp., *Syntrophomonas wolfei*, *Thermophilic cyanobacteria*, *Thermus thermophilus*, *Thiobacillus* A2, *Thiobacillus* sp., *Thiocapsa* sp., *Thraustochytrium* sp., *Thiocystis violacea*, *Vibrio parahaemolyticus*, *Xanthobacter autotrophicus*, *Xanthomonas maltophilia*, *Zoogloea* sp., and microorganisms transformed with a gene encoding an enzyme having the ability to produce oil. In addition, it is obvious that any microorganisms capable of producing oil may also be used in the method of the present invention.

In the present invention, the culture in step (a) may comprise first-step culture for microbial cell growth and second-step culture for oil production, in which the culture for oil production is preferably carried out in a medium containing a limited nitrogen source in order to increase the production of oil.

The oil produced by the microorganisms is autolysed in the microorganisms, and the autolysis in step (b) may be carried out by lipase. Examples of the lipase include triacyl glycerol lipase (EC: 3.1.1.34, 3.1.1.13), monoacylglycerol lipase (EC: 3.1.1.23), and lysophospho lipase (EC: 3.1.1.5).

Preferably, a gene encoding lipase may be introduced or amplified in the microorganisms having the ability to produce oil. More preferably, a lipase gene that may be activated by reaction with a substrate may be introduced in the microorganisms. In one Example of the present invention, for the autolysis of oil in microorganisms, a microbial strain introduced with lipase genes of SEQ ID NOS: 5 and 8 was used. In another Example of the present invention, a microbial strain introduced with triacylglycerol lipase genes of SEQ ID NOS: 17, 18 and 19 alone or a monoacylglycerol lipase gene recognized by SEQ ID NOS: 13 and 14 alone or a combination thereof was used.

In the present invention, the alcohol that is added in step (c) may be a primary alcohol, a secondary alcohol or a tertiary alcohol. Preferably, an alcohol having 1 to 8 carbon atoms or a mixture of two or more of alcohols having 1 to 8 carbon atoms may be used. More preferably, methanol may be used.

In addition, the reaction in step (c) may be carried out at 80-120° C. for 1-24 hours. Also, the reaction in step (c) may be carried out in the presence of an organic solvent, preferably chloroform.

In one Example of the present invention, *Rhodococcus opacus* PD630 was used as a microbial strain having the ability to produce oil, and a two-step culture process consisting of first-step culture for microbial cell growth and second-step culture for oil production was performed. In the second-step culture for oil production, a medium with a limited nitrogen source was used to induce the production of oil. For the autolysis of the produced oil, a lipase gene that is activated by acetamide was introduced into the microbial strain, and the lipase activated by adding acetamide to the microorganisms was used to produce about 0.27 g/L of free fatty acid in vivo.

In addition, the obtained free fatty acid solution was freeze-dried to remove water, after chloroform and $H_2SO_4$-containing methanol were added thereto and allowed to react at 100° C. for 12 hours. Then, water was added thereto and the organic solvent layer was separated, thereby obtaining free fatty acid methyl ester. The concentration of the produced free fatty acid methyl ester was 0.2 g/L, suggesting that the conversion of the free fatty acid into the free fatty acid methyl ester was achieved (FIG. 1). This demonstrated that the use of the method according to the present invention allows a fatty acid methyl ester to be produced with high efficiency in an easier and environmentally friendly method, indicating that the method of the present invention is very useful for the production of biodiesel as a substitute for light oil or the like.

In another aspect, the present invention is directed to a method for producing a fatty acid methyl ester using microorganisms having the ability to produce oil and containing a gene encoding lipase, the method comprising the steps of:

(a) culturing microorganisms having the ability to produce oil and containing a gene encoding lipase, thus producing oil;

(b) inducing the autolysis of the produced oil by lipase in the microorganisms to produce a free fatty acid; and (c) adding methanol to the produced free fatty acid and reacting the methanol with the free fatty acid to produce a fatty acid methyl ester.

In another Example of the present invention, a microbial strain introduced with a triacylglycerol lipase gene alone or a monoacylglycerol lipase gene alone or a combination thereof was used, and then it was seen that, when the triacylglycerol lipase gene and the monoacylglycerol lipase gene were introduced together into the microbial strain, a larger amount of free fatty acid was produced from the same amount of glucose compared when the triacylglycerol lipase gene or the monoacylglycerol lipase gene was introduced, and that a fatty acid methyl ester was produced with higher efficiency when the triacylglycerol lipase gene and the monoacylglycerol lipase gene were introduced together. Thus, in the present invention, the triacylglycerol lipase gene and the monoacylglycerol lipase gene are preferably introduced together into a microbial strain.

Meanwhile, the following examples of the present invention illustrate only specific media and culture methods, it will be obvious to those skilled in the art to use a glycolytic solution such as whey or CSL (corn steep liquor), and other media, and use various culture methods, such as fed-batch culture or continuous culture, as reported in the literature (Lee at al., *Bioprocess Biosyst. Eng.*, 26: 63, 2003; Lee et al., *Appl. Microbiol. Biotechnol.*, 58: 663, 2002; Lee et al., *Biotechnol. Lett.*, 25: 111, 2003; Lee et al., *Appl. Microbiol. Biotechnol.*, 54: 23, 2000; Lee et al., *Biotechnol. Bioeng.*, 72: 41, 2001).

EXAMPLES

Hereinafter, the present invention will be described in further detail with reference to examples. It will be obvious to a person having ordinary skill in the art that these examples are illustrative purposes only and are not to be construed to limit the scope of the present invention.

Particularly, although the following examples illustrate only a method in which *Rhodococcus opacus* PD630 is used as a host microorganism, it will be obvious to a person skilled in the art from the disclosure herein that any microorganism having the ability to produce oil or any microorganism transformed so as to have the ability to produce oil may be used in the method of the present invention.

In addition, although the following examples illustrate that methanol is used as alcohol in a process of esterifying a free fatty acid, it will be obvious to a person skilled in the art that other alcohols may be used to esterify free fatty acids, thereby producing various kinds of fatty acid alkyl esters.

Example 1

Figure 2A:
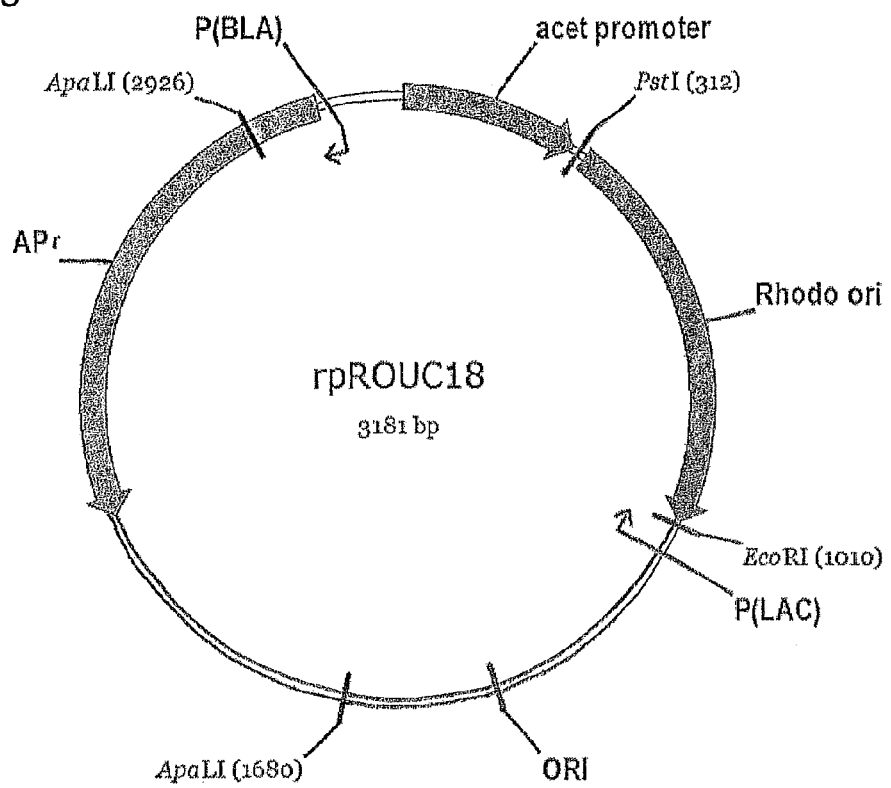
FIG. 2 shows genetic maps of the recombinant vectors rpROUC18 (a) and rpROUC18_KM (b).
Figure 2B:
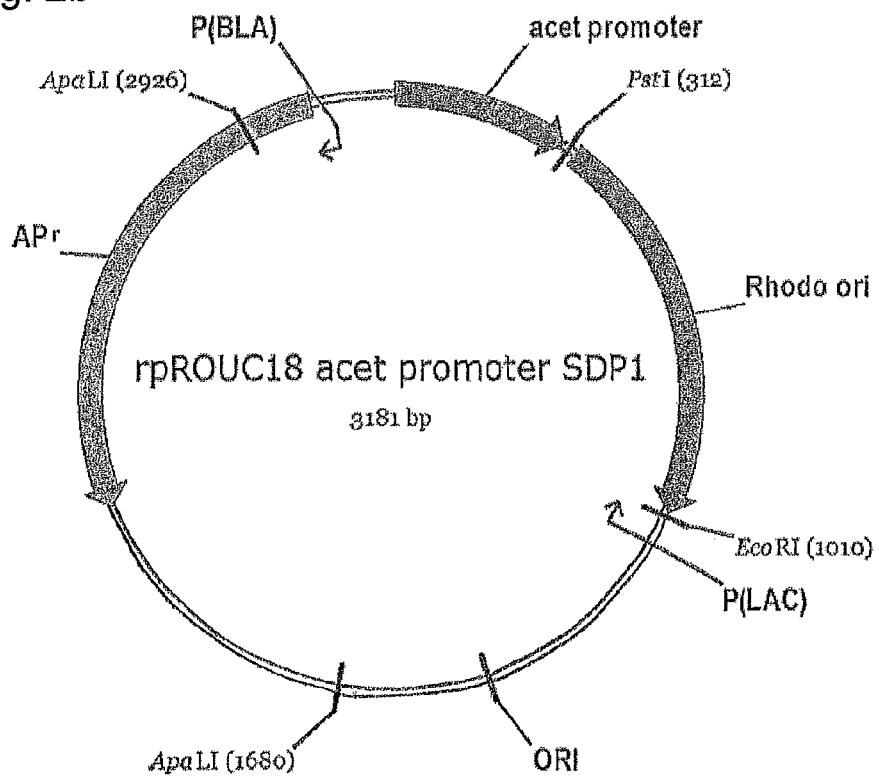

Preparation (1) of Recombinant Strain *Rhodococcus opacus* PD630 Introduced with Genes Inducing the Autolysis of Oil 1-1. Construction of Plasmid pRUCSdp A recombinant vector of rpROUC18 (SEQ ID NO: 1) and a recombinant vector of rpROUC18_KM (SEQ ID NO: 2), which have the genetic maps shown in FIG. 2, were prepared from a pUC18 plasmid (Phamacia, Biotech, Uppsala, Sweden), and then gene fragments were introduced therein in the following manner.

First, PCR was performed using the genomic DNA of *Arabidopsis thaliana* col. as a template with synthesized primers of SEQ ID NOS: 3 and 4, thereby constructing an sdp1 gene fragment encoding triacylglycerol lipase.

```
SEQ ID NO: 3:    5'-TATAGGCGCCATGGATATAAGTAATGAGGC-3'

SEQ ID NO: 4:    5'-TGTCCTGCAGCTAAGCATCTATAACACTAC-3'
```

Then, the prepared sdp1 fragment (SEQ ID NO: 5) was treated with restriction enzymes (NarI and PstI) and then ligated into a rpROUC18 plasmid (Phamacia, Biotech, Uppsala, Sweden) by T4 DNA ligase, thereby constructing the recombinant plasmid pRUCSdp.

1-2. Construction of Plasmid pRUCSdpMag

PCR was performed using the genomic DNA of *Mycobacterium smegmatis* (KCTC 9108) as a template with synthesized primers of SEQ ID NOS: 6 and 7, thereby constructing an MSMEG_0220 gene fragment encoding monoacylglycerol lipase.

```
SEQ ID NO: 6:
5'-

TATATCTAGAACAACGGGGAGGACAACCGAATGGTGAGCAG
CACCCGCAGTGAACAC-3'

SEQ ID NO: 7:
5'-TATATCTAGATCACAGATGACTCACGATCCATGAG-3'
```

Figure 3:
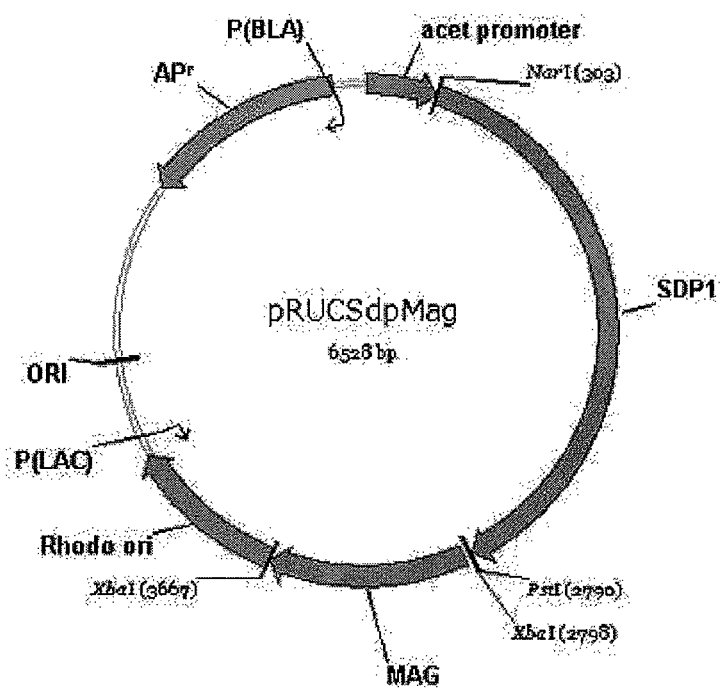
FIG. 3 shows a genetic map of the recombinant vector pRUCSdpMag containing the sdp1 and MSMEG_0220 genes.

Then, the prepared MSMEG_0220 fragment (SEQ ID NO: 8) was treated with a restriction enzyme (XbaI) and then ligated into a pRUCSdp plasmid by T4 DNA ligase, thereby constructing the recombinant plasmid pRUCSdpMag shown in FIG. 3. Then, the prepared recombinant plasmid pRUCSdpMag was introduced into a *Rhodococcus opacus* PD630 DSM 44193 strain (Deutsche Sammlung von Mikroorganismen and Zellkulturen (DSMZ), Germany), thereby constructing a recombinant strain introduced with a lipase gene that is activated by acetamide.

Example 2

Preparation (2) of Recombinant Strains of Rhodococcus opacus PD630 Introduced with Genes Inducing the Autolysis of Oil

2-1. Construction of Plasmids

Using the primers, conditions and gene templates shown in Table 1 below, various plasmids as shown in FIG. 4 were constructed by introducing triacylglycerol lipase and monoacylglycerol lipase into the rpROUC18 plasmid and a rpROUC18_KM plasmid of Example 1-1. In addition, triacylglycerol lipase and monoacylglycerol lipase were also introduced together into the plasmids. Table 1 below indicates the types of restriction enzymes and the origins of genes, and in addition, various kinds of genes may be introduced.

As described in Example 1, a promoter that is induced by acetamide was used in the rpROUC18 plasmid such that the introduced gene could be operated at the desired time, in which the acetamide was used at a concentration of 0.5% (w/w).

```
ARAT_f primer
                                        (SEQ ID NO: 9)
5'-TATATTCCATGGGGAGGACAACATATAAGTAATGAGGCTAGT-3'

ARAT-r primer
                                       (SEQ ID NO: 10)
5'-CCGCCTGCAGCTAAGCATCTATAACACTAC-3'

ATAG7_f primier
                                       (SEQ ID NO: 11)
5'-TATTGACGTCGACAACGGGGAGGACAACCGAATGGAACGCGGATCCA

CTTG-3'

ATAG7-r primer
                                       (SEQ ID NO: 12)
5'-CTTGTACTAAGTCCCGGGTTAGTGGACGACCTCGAAGC-3'

Mlip2_f primer
                                       (SEQ ID NO: 13)
5'-

TATTGGCGCCGACAACGGGGAGGACAACCGAATGGTGAGCAGCACCCGCA

GTGAA-3'

Mlip2r primer
                                       (SEQ ID NO: 14)
5'-CCACGATGGACACGTTGTACTAAGTCTGCAGTCACAGATGACTCACG

ATCC-3'

PAO_f primer
                                       (SEQ ID NO: 15)
5'-TATAGACGTCATGAAGAAGAAGTCTCTGCTCCCC-3'

PAO_r primer
                                       (SEQ ID NO: 16)
5'-TCGAaagcttCTACAGGCTGGCGTTCTTCA-3'
```

TABLE 1

| Gene | Primer | Restriction enzyme site contained in the primer | Reaction condition |
| --- | --- | --- | --- |
| TAG lipase of Arabidopsis thaliana | ARAT_f<br>ARAT_r | NcoI<br>PstI | Cycle I: 94° C., 5 min<br>Cycle II: (30 cycles)<br>94° C., 40 sec<br>56° C., 30 sec |
| TAG lipase of Aspergillus fumigatus | ATAG7-f<br>ATAG7-r | AatII<br>XmaI | 72° C., 1 min<br>Cycle III: 72° C., 5 min<br>Cycle IV: 4° C., store |
| TAG lipase of Pseudomonas aeruginosa | PAO_f<br>PAO_r | AatII<br>HindIII | |
| MAG lipase of Mycobacterium smegmatis | Mlip2_f<br>Mlip2_r | NarI<br>PstI | Cycle I: 94° C., 5 min<br>Cycle II: (30 cycles)<br>94° C., 40 sec<br>56° C., 30 sec<br>72° C., 2 min<br>Cycle III: 72° C., 5 min<br>Cycle IV: 4° C., store |

In FIG. 4, the *Arabidopsis thaliana* TAG lipase gene fragment introduced into the rpROUC18KM_Ara plasmid and the rpROUC18KM_Ara_MAG plasmid has a nucleotide sequence of SEQ ID NO: 17, and the *Aspergillus fumigatus* TAG 7G lipase gene fragment introduced into the rpROUC18KM_Af7G plasmid and the rpROUC18KM_Af7G_MAG plasmid has a nucleotide sequence of SEQ ID NO: 18. Also, the *Pseudomonas aeruginosa* TAG lipase gene fragment introduced into the rpROUC18KM_PAO plasmid and the rpROUC18KM_PAO_MAG plasmid has a nucleotide sequence of SEQ ID NO: 19, and the *M. smegmatis* MAG lipase gene fragment introduced into the rpROUC18KM_MAG plasmid, the rpROUC18KM_Ara_MAG plasmid, the rpROUC18KM_Af7G_MAG plasmid and the rpROUC18KM_PAO_MAG plasmid has a nucleotide sequence recognized by SEQ ID NOS: 13 and 14.

Example 3

Production of Fatty Acid Methyl Ester Using Recombinant Strain of Rhodococcus opacus PD630

3-1: Production (1) of Free Fatty Acid Using the Recombinant Strain of *Rhodococcus opacus* PD630 of Example 1

In order to culture the recombinant strain of *Rhodococcus opacus* PD630 of Example 1, introduced with the lipase gene that is activated by acetamide, two-step culture was performed in a medium having a limited nitrogen source in order to produce oil.

First, in first-step culture, the recombinant strain of Example 1 was cultured in a 250-ml flask containing 100 ml of NB (nutrient broth) at 30° C. and 250 rpm for 24 hours.

The culture broth was centrifuged at 6000 rpm for 10 minutes to collect the microbial cells which were then washed with MSM medium (which is used in second-step culture) to remove the NB component. Then, the cell solution was centrifuged at 6000 rpm for 10 minutes to collect the microbial cells which were then suspended in 100 ml of MSM medium. The composition of the MSM medium (pH 7.0) was as follows: per liter of distilled water, 0.8 g $KH_2PO_4$, 5.58 g $Na_2HPO_4$, 0.1 g $(NH_4)_2SO_4$, 0.12 g $MgSO_47H_2O$, 0.5 mg $FeSO_45H_2O$, 1.54 mg $MnSO_45H_2O$, 2.86 mg $H_3BO_3$, 0.039 mg $CuSO_45H_2O$, 0.041 mg $CoCl_26H_2O$, 0.021 mg $ZnCl_2$, 0.025 mg $Na_2MoO_42H_2O$, and 11.6 mg $CaCl_22H_2O$.

20 g/l of glucose as a carbon source was added to the microbial cells suspended in 100 ml of the MSM medium, after which the microbial cells were cultured at 30° C. and 250 rpm for 24 hours. Then, the accumulation of oil in the microbial strain was checked in real-time by microscopic monitoring. Then, in order to activate lipase to produce free fatty acid, 0.5% (w/v) of acetamide was added to the microbial cells which were then cultured at 30° C. for 48 hours.

After completion of the culture, the culture broth was centrifuged at 6000 rpm for 10 minutes to collect the cells. The collected cells were washed once with distilled water, and then dried in a dryer at 100° C. for 24 hours.

The dried cells were analyzed by gas chromatography using an Agilent 6890N series gas chromatography system (Chiraldex G-TA of Astec, USA) equipped with a capillary column, thereby measuring the content of synthesized free fatty acid in the cells. The results of the two-step flask culture indicated that the free fatty acid was produced at a concentration of 0.27 g/l.

3-2: Production (2) of Free Fatty Acid Using the Recombinant Strain of *Rhodococcus opacus* PD630 of Example 2

In order to culture the recombinant strains of *Rhodococcus opacus* PD630 of Example 2, introduced with the lipase gene that is activated by acetamide, two-step culture was performed in a medium having a limited nitrogen source in order to produce oil.

First, in first-step culture, each of the recombinant strains of Example 2 was cultured in a 250-ml flask containing 200 ml of TSB (tryptic soy broth) at 30° C. and 200 rpm for 16 hours.

The culture broth was centrifuged at 3000 rpm for 30 minutes to collect the microbial cells which were then washed with MSM medium to remove the TSB component. Then, the cell solution was centrifuged at 3000 rpm for 30 minutes to collect the microbial cells which were then suspended in 200 ml of MSM medium. The composition of the MSM medium (pH 7.0) was as follows: per liter of distilled water, 0.8 g $KH_2PO_4$, 5.58 g $Na_2HPO_4$, 0.1 g $(NH_4)_2SO_4$, 0.12 g $MgSO_4 7H_2O$, 1.0 mg $FeSO_4 5H_2O$, 3.08 mg $MnSO_4 5H_2O$, 5.72 mg $H_3BO_3$, 0.078 mg $CuSO_4 5H_2O$, 0.082 mg $CoCl_2 6H_2O$, 0.042 mg $ZnCl_2$, 0.050 mg $Na_2MoO_4 2H_2O$, and 23.2 mg $CaCl_2 2H_2O$.

20 g/l of glucose as a carbon source was added to the microbial cells suspended in 200 ml of the MSM medium, after which the microbial cells were cultured at 30° C. and 200 rpm for 48 hours. Then, the accumulation of oil in the microbial strain was checked in real-time by microscopic monitoring. Then, in order to activate lipase to produce free fatty acid, 0.5% (w/v) of acetamide was added to the microbial cells which were then cultured at 30° C. for 24 hours.

After completion of the culture, the culture broth was centrifuged at 3,000 rpm for 30 minutes to collect the cells. The supernatant was freeze-dried at −45° C. and 10 mmTorr for 48 hours. The collected cells were washed once with distilled water, and then dried in a dryer at 80° C. for 24 hours. 0.1 g of each of the resulting materials was taken and treated using a microbial identification system (Microbial ID, Inc., Network, Del., USA) according to the manufacturer's instruction, thus preparing gas chromatography samples.

Each of the prepared samples was analyzed by gas chromatography using an Agilent 6890N series gas chromatography system (Chiraldex G-TA of Astec, USA) equipped with a capillary column, thereby measuring the content of synthesized free fatty acid in the cells.

The results of the 2-step flask culture as described above indicated that the content of free fatty acid in the supernatant was significantly higher than the content of free fatty acid in the cells, suggesting that the free fatty acid was secreted extracellularly. FIG. 5 shows the results of measuring the free fatty acid in the freeze-dried supernatant. As can be seen in FIG. 5, the free fatty acid was produced as a mixture of free fatty acids having various lengths. In addition, it could be seen that, when triacylglycerol lipase was introduced together with monoacylglycerol lipase, a larger amount of the free fatty acid was produced from the same amount of glucose compared to when triacylglycerol lipase alone was introduced.

3-3: Conversion of Free Fatty Acid into Fatty Acid Methyl Ester

To the dried microbial strain obtained in Example 3-1, 2 ml of chloroform was added and 1 ml of methanol containing 3% (v/v) $H_2SO_4$ was added. The mixture was allowed to react at 100° C. for 12 hours.

After completion of the reaction, the mixture was cooled to room temperature, and 1 ml of distilled water was added to the mixture which was then intensively stirred for 5 minutes, whereby the mixture was separated into an organic solvent (chloroform) layer and a water (aqueous solution) layer. The resulting material was centrifuged at 10,000 rpm for 10 minutes, and only the organic solvent layer was collected and analyzed by gas chromatography using an Agilent 6890N series gas chromatography system (Chiraldex G-TA of Astec, USA) equipped with a capillary column, thereby measuring the concentration of produced fatty acid methyl ester in the organic solvent layer.

Figure 6:
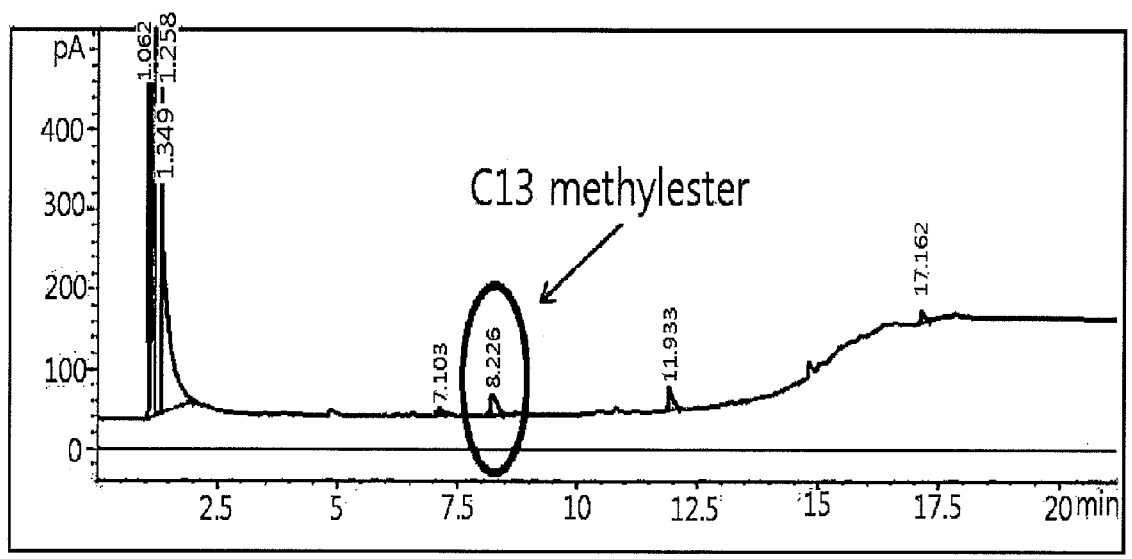

As a result, as shown in FIG. 6, it was found that a C13 fatty acid methyl ester was produced at a concentration of 0.2 g/L. This suggests that the free fatty acid was converted into the fatty acid methyl ester.

In addition, the same methanol as described above was added to and reacted with the supernatant obtained in Example 3-2, and then the concentration of produced fatty methyl ester in the reaction solution was measured.

As a result, as can be seen in FIG. 7, the free fatty acid was converted into fatty acid methyl ester. Particularly, it could be seen that, when triacylglycerol lipase (TAG lipase) and monoacylglycerol lipase (MAG lipase) were introduced together, a significantly larger amount of fatty acid methyl ester was produced compared to when triacylglycerol lipase (TAG lipase) or monoacylglycerol lipase (MAG lipase) was introduced alone. As described above, the method of producing fatty acid alkyl ester using microorganisms according to the present invention shows high production efficiency such that it can be immediately used for the production of biofuel. Also, it could be seen that the fatty acid methyl ester production efficiency of the present invention was significantly higher than that of an existing method known in the art.

In other words, it was demonstrated that the use of the method according to the present invention allows a fatty acid methyl ester to be produced with high efficiency in an easier and environmentally friendly method, indicating that the method of the present invention is very useful for the production of biodiesel as a substitute for light oil or the like.

INDUSTRIAL APPLICABILITY

As described above, according to the method of the present invention, oil accumulated in microorganisms, such as triacylglycerol that is typical oil produced by microorganisms, can be converted into a fatty acid alkyl ester with high efficiency using a metabolic engineering approach. Thus, the method of the present invention is useful for the industrial production of a fatty acid alkyl ester which has been recently found to be effective as biodiesel.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of producing a fatty acid alkyl ester, the method comprising:
   providing *Rhodococcus opacus* transformed with a first gene encoding a triacyl glycerol lipase and a second gene encoding a monoacyl glycerol lipase;
   culturing *Rhodococcus opacus* in a culture medium to produce oil and free fatty acids in the culture medium; and
   causing an alcohol to contact the free fatty acids for producing fatty acid alkyl esters,
   wherein the first gene comprises SEQ ID NO: 19, and the second gene comprises *M. smegmatis* MAG lipase gene produced by PCR amplification of *M. smegmatis* genomic DNA with the primers of SEQ ID NO: 13 and SEQ ID NO: 14.

2. The method of claim 1, wherein the oil is selected from the group consisting of triacylglycerol (TAG), diacylglycerol (DAG), monoacylglycerol (MAG), phospholipid, lipid, sphingolipid and saccharolipid.

3. The method of claim 1, wherein the free fatty acid is selected from the group consisting of oleic acid, linoleic acid, linolenic acid, palmitoleic acid, ricinoleic acid, vaccenic acid, gadoleic acid, arachidonic acid, EPA (5,8,11,14,17-eicosapentaenoic acid), erucic acid, DHA (4,7,10,13,16,19-docosahexaenoic acid), butyric acid, caproic acid, caprylic acid, capric acid, lauric acid, myristic acid, palmitic acid, stearic acid, arachidic acid, behenic acid and lignoceric acid.

4. The method of claim 1, wherein the free fatty acid comprises at least one substituent group selected from the group consisting of an aromatic ring group, an epoxy group, a cyano group and a halogen group.

5. The method of claim 1, wherein the alcohol contacts the free fatty acids at a temperature of 80-120° C.

* * * * *

SEQUENCE LISTING

<160> NUMBER OF SEQ ID NOS: 20

<210> SEQ ID NO 1
<211> LENGTH: 3181
<212> TYPE: DNA
<213> ORGANISM: Artificial sequence
<220> FEATURE:
<223> OTHER INFORMATION: Synthetic sequence of rpROUC18 plasmid

<400> SEQUENCE: 1

```
gatctaccgg ttccacgagg cgctcaacgt gtacgggcct gcgctcaagg aactcatcca    60
cgaagagttc ggtgacggca tcatgagcgc catcaacttc aaggtggaca tccagcgtcg   120
tcccgatcca gacggggacc gggtggtggt gaccttcgac gggaagttcc tcgactaccg   180
ctggtagtcc gacgcgtgcg tcaattctgg ctgatgtcaa cgggttcgaa cgcaaccgca   240
acgtcgtcgc aacatggcgt gggtagcttc gggcccgtcg acaacgggga ggacaaccga   300
ggcgccctgc aggtcgactc tagacggcat cttgcccaga ttttcccag gtaagagcgc    360
gtctcattgc caaagatttg cgactgtgcc gaatgagact gtcgggcgtc tcattccccc   420
acgtcgggcc gtctcgaaag tcagtcgcat tagaccggct catttgttgc tcaatgcgcc   480
gacttatgag actgttgagt catgacagac accgcgaaca tccccgcccc gaccggacgc   540
acattcggat acgcccgcgt ctcgacttcc cggcagaacc ttgaccgcca gatggacacg   600
ctccgcaaga tgggcgtgga cggcgaccgg atctatgccg ataaggtgac cggccgcacg   660
atggaccgcc ccgcgtggca ggtctgcaac tcgcatctgg atgccggcga cacgctcgtg   720
gtggacgcac tcgaccgttt gggacgctcc acgttggagg tcatcgacac aatccacgac   780
ctgaccgaac gcggcgtcat catcgtggac cgcacgtacc gccgcctaga tgccagtgac   840
gcggtcggga aggcgttggt gcagatcatg gcggtcatgg ccgagatgga agtcaacttg   900
aaagccgagc gtgccgccgc tgctcgtgag tccgccgccg cccgtggaaa gcacaccgga   960
cgcccccgca agctcgccaa ccacgacgtt gctcgtgccc gtgagctcga attcgtaatc  1020
atggtcatag ctgtttcctg tgtgaaattg ttatccgctc acaattccac acaacatacg  1080
agccggaagc ataaagtgta aagcctgggg tgcctaatga gtgagctaac tcacattaat  1140
tgcgttgcgc tcactgcccg ctttccagtc gggaaacctg tcgtgccagc tgcattaatg  1200
aatcggccaa cgcgcgggga gaggcggttt gcgtattggg cgctcttccg cttcctcgct  1260
cactgactcg ctgcgctcgg tcgttcggct gcggcgagcg gtatcagctc actcaaaggc  1320
ggtaatacgg ttatccacag aatcagggga taacgcagga agaacatgt gagcaaaagg   1380
ccagcaaaag gccaggaacc gtaaaaaggc cgcgttgctg gcgttttcc ataggctccg   1440
cccccctgac gagcatcaca aaaatcgacg ctcaagtcag aggtggcgaa acccgacagg  1500
actataaaga taccaggcgt ttccccctgg aagctccctc gtgcgctctc ctgttccgac  1560
cctgccgctt accggatacc tgtccgcctt tctcccttcg ggaagcgtgg cgctttctca  1620
tagctcacgc tgtaggtatc tcagttcggt gtaggtcgtt cgctccaagc tgggctgtgt  1680
gcacgaaccc ccgttcagc ccgaccgctg cgccttatcc ggtaactatc gtcttgagtc   1740
caacccggta agacacgact tatcgccact ggcagcagcc actggtaaca ggattagcag  1800
agcgaggtat gtaggcggtg ctacagagtt cttgaagtgg tggcctaact acggctacac  1860
tagaaggaca gtatttggta tctgcgctct gctgaagcca gttaccttcg gaaaaagagt  1920
tggtagctct tgatccggca aacaaaccac cgctggtagc ggtggttttt ttgtttgcaa  1980
gcagcagatt acgcgcagaa aaaaaggatc tcaagaagat cctttgatct tttctacggg  2040
```

```
gtctgacgct cagtggaacg aaaactcacg ttaagggatt ttggtcatga gattatcaaa    2100
aaggatcttc acctagatcc ttttaaatta aaaatgaagt tttaaatcaa tctaaagtat    2160
atatgagtaa acttggtctg acagttacca atgcttaatc agtgaggcac ctatctcagc    2220
gatctgtcta tttcgttcat ccatagttgc ctgactcccc gtcgtgtaga taactacgat    2280
acgggagggc ttaccatctg gccccagtgc tgcaatgata ccgcgagacc cacgctcacc    2340
ggctccagat ttatcagcaa taaaccagcc agccggaagg gccgagcgca gaagtggtcc    2400
tgcaacttta tccgcctcca tccagtctat taattgttgc cgggaagcta gagtaagtag    2460
ttcgccagtt aatagtttgc gcaacgttgt gccattgct acaggcatcg tggtgtcacg     2520
ctcgtcgttt ggtatggctt cattcagctc cggttcccaa cgatcaaggc gagttacatg    2580
atcccccatg ttgtgcaaaa aagcggttag ctccttcggt cctccgatcg ttgtcagaag    2640
taagttggcc gcagtgttat cactcatggt tatggcagca ctgcataatt ctcttactgt    2700
catgccatcc gtaagatgct tttctgtgac tggtgagtac tcaaccaagt cattctgaga    2760
atagtgtatg cggcgaccga gttgctcttg cccggcgtca atacgggata ataccgcgcc    2820
acatagcaga actttaaaag tgctcatcat tggaaaacgt tcttcgggc gaaaactctc     2880
aaggatctta ccgctgttga tccagttc gatgtaaccc actcgtgcac ccaactgatc     2940
ttcagcatct tttactttca ccagcgtttc tgggtgagca aaaacaggaa ggcaaaatgc    3000
cgcaaaaaag ggaataaggg cgacacggaa atgttgaata ctcatactct ccttttttca    3060
atattattga agcatttatc agggttattg tctcatgagc ggatacatat ttgaatgtat    3120
ttagaaaaat aaacaaatag gggttccgcg cacatttccc cgaaaagtgc cacctgacgt    3180
c                                                                   3181
```

<210> SEQ ID NO 2
<211> LENGTH: 6625
<212> TYPE: DNA
<213> ORGANISM: Artificial sequence
<220> FEATURE:
<223> OTHER INFORMATION: Synthetic sequence of rpROUC18_KM plasmid

<400> SEQUENCE: 2

```
cgcaccgatc gcccttccca acagttgcgg ggggggggg aaagccacgt tgtgtctcaa      60
aatctctgat gttacattgc acaagataaa aatatatcat catgaacaat aaaactgtct    120
gcttacataa acagtaatac aaggggtgtt atgagccata ttcaacggga acgtcttgc     180
tcgaggccgc gattaaattc caacatggat gctgatttat atgggtataa atgggctcgc    240
gataatgtcg ggcaatcagg tgcgacaatc tatcgattgt atgggaagcc cgatgcgcca    300
gagttgtttc tgaaacatgg caaaggtagc gttgccaatg atgttacaga tgagatggtc    360
agactaaact ggctgacgga atttatgcct cttccgacca tcaagcattt tatccgtact    420
cctgatgatg catggttact caccactgcg atccccggga aaacagcatt ccaggtatta    480
gaagaatatc ctgattcagg tgaaaatatt gttgatgcgc tggcagtgtt cctgcgccgg    540
ttgcattcga ttcctgtttg taattgtcct tttaacagcg atcgcgtatt tcgtctcgct    600
caggcgcaat cacgaatgaa taacggtttg gttgatgcga gtgattttga tgacgagcgt    660
aatggctggc ctgttgaaca agtctggaaa gaaatgcata agcttttgcc attctcaccg    720
gattcagtcg tcactcatgg tgatttctca cttgataacc ttattttgga cgaggggaaa    780
ttaataggtt gtattgatgt tggacgagtc ggaatcgcag accgatacca ggatcttgcc    840
```

```
atcctatgga actgcctcgg tgagttttct ccttcattac agaaacggct tttcaaaaa        900
tatggtattg ataatcctga tatgaataaa ttgcagtttc atttgatgct cgatgagttt        960
ttctaagatc taccggttcc acgaggcgct caacgtgtac gggcctgcgc tcaaggaact       1020
catccacgaa gagttcggtg acggcatcat gagcgccatc aacttcaagg tggacatcca       1080
gcgtcgtccc gatccagacg gggaccgggt ggtggtgacc ttcgacggga agttcctcga       1140
ctaccgctgg tagtccgacg cgtcgtcaa ttctggctga tgtcaacggg ttcgaacgca        1200
accgcaacgt cgtcgcaaca tggcgtgggt agcttcgggc ccgtcgacaa cggggaggac       1260
aaccgaggcg ccatggatat aagtaatgag gctagtgtcg atccctttc gattggacca        1320
tcatctatca tgggtcgaac cattgctttc agagtcttgt tctgtagatc aatgtcacag       1380
cttaggcgtg atctctttcg gttcttgttg cattggtttc ttagatttaa gctgaccgtt       1440
tcaccgtttg tgtcgtggtt tcatcctcgg aaccctcaag ggattttagc ggtggttaca       1500
atcattgcct ttgtgttgaa acgatacacg aatgtgaaaa taaggcgga aatggcttac        1560
cggaggaagt tttggaggaa tatgatgcgg acggctttga cttatgagga atgggctcat       1620
gctgctaaga tgttagagaa ggaaacacca aagatgaatg aatctgatct ttatgatgaa       1680
gagttggtta agaacaagct tcaggagctt cgtcatcgtc gccaagaagg ctcacttaga       1740
gacattatgt tttgtatgag agctgatttg gtgaggaatc tcggtaatat gtgtaattcg       1800
gagcttcata aggtagact tcaggttcct agacatatca aagagtacat tgatgaggtg        1860
tctactcagt tgagaatggt ttgtaactct gattcagagg agctttcttt agaagagaag       1920
cttttcttta tgcatgaaac acggcatgcc tttggtagaa cggcttttgct tttgagtggt       1980
ggggcttctc ttggtgcgtt tcatgttggt gtggttagga ctttggttga gcataagctt       2040
ttacctcgaa taattgctgg ttctagtgtt ggatccatca tttgtgctgt tgtggcctca       2100
aggtcttggc cagaactaca gagtttcttt gagaattctt tgcattcttt acagttcttt       2160
gatcagctcg gaggcgtgtt ctcaatagtg aaacgggtaa tgacacaagg ggctctacac       2220
gatatcagac agttgcaatg tatgcttaga aacctcacaa gcaatctcac attccaagaa       2280
gcttatgaca tgacaggaag gattctcggg atcaccgttt gctccccaag aaagcatgaa       2340
cctcctcggt gtcttaacta tttgacttcg cctcatgtgg ttatatggag cgcagtgact       2400
gcttcttgtg cttttcctgg tctctttgaa gctcaagagc taatggctaa agatcgaagt       2460
ggagagatcg taccgtatca tccacctttc aatttggatc cagaagtagg cactaaatca       2520
tcatctggac gccggtggag agatggtagt ttggaggttg atttaccaat gatgcagctt       2580
aaagaactgt tcaatgtcaa tcattttatt gtgagccaag ccaatcctca cattgctcca       2640
ttactgcgtc taaaggattt agttcgagct tatggtggta gattcgcagc taagctcgcg       2700
catctagtgg agatggaggt caaacataga tgcaaccagg tattagagct cggttttcct       2760
ctcggtggac tcgcaaagct tttgctcag gagtgggaag gtgatgttac agttgtaatg        2820
cctgctactc ttgctcagta ctcgaagatt atacaaaatc cgactcatgt cgagcttcag       2880
aaagcggcta accaaggaag aagatgcact gggagaagc tctcagccat aaaatcaaac        2940
tgcgggatcg agcttgcgct tgatgattct gtagctattc ttaaccatat gcggaggctc       3000
aagaaaagtg cggagagagc cgccactgcc acgtcttcgt ctcatcacgg attggcttca       3060
accaccagat tcaatgcttc aagaagaatc ccatcttgga acgtccttgc cagagagaac       3120
tcaacaggct cactggatga tctagtcact gacaataacc tccacgcttc ttcgggcagg       3180
aatttaagcg acagtgaaac agagagcgtg gagttgagtt cttggacaag aactggtgga       3240
```

```
cctttaatga gaacagcttc tgctaataag ttcattgatt ttgttcagag tcttgatatc   3300
gacattgcat tggtcagagg atttagtagc agtcccaatt ctccagcagt tcctcctggt   3360
ggctcgttta ctccaagccc gagatccata gcggctcatt cggatatcga atcaaacagc   3420
aatagcaaca atcttggaac aagcacttca agcataacag ttactgaagg tgatcttcta   3480
cagcctgaga gaacgagtaa cggatttgtg ttaaacgtcg ttaaaagaga gaacttggga   3540
atgccatcga ttgggaacca aaatacagag ttaccagaga gtgtacagct cgatataccg   3600
gagaaggaga tggattgtag ctctgtatca gaacacgaag aagatgataa cgacaatgaa   3660
gaagaacata acggctcgag tctggttact gtttcttcag aagattccgg tttacaagaa   3720
ccggtgtctg gtagtgttat agatgcttag ctgcaggtcg actctagacg gcatcttgcc   3780
cagatttttc ccaggtaaga gcgcgtctca ttgccaaaga tttgcgactg tgccgaatga   3840
gactgtcggg cgtctcattc ccccacgtcg ggccgtctcg aaagtcagtc gcattagacc   3900
ggctcatttg ttgctcaatg cgccgactta tgagactgtt gagtcatgac agacaccgcg   3960
aacatccccg ccccgaccgg acgcacattc ggatacgccc gcgtctcgac ttcccggcag   4020
aaccttgacc gccagatgga cacgctccgc aagatgggcg tggacggcga ccggatctat   4080
gccgataagg tgaccggccg cacgatggac cgccccgcgt ggcaggtctg caactcgcat   4140
ctggatgccg cgacacgct cgtggtggac gcactgacc gtttgggacg ctccacgttg   4200
gaggtcatcg acacaatcca cgacctgacc gaacgcggcg tcatcatcgt ggaccgcacg   4260
taccgccgcc tagatgccag tgacgcggtc gggaaggcgt tggtgcagat catggcggtc   4320
atggccgaga tggaagtcaa cttgaaagcc gagcgtgccg ccgctgctcg tgagtccgcc   4380 gccgccgtg gaaagcacac cggacgcccc cgcaagctcg ccaaccacga cgttgctcgt   4440
gcccgtgagc tcgaattcgt aatcatggtc atagctgttt cctgtgtgaa attgttatcc   4500
gctcacaatt ccacacaaca tacgagccgg aagcataaag tgtaaagcct ggggtgccta   4560
atgagtgagc taactcacat taattgcgtt gcgctcactg cccgctttcc agtcgggaaa   4620
cctgtcgtgc cagctgcatt aatgaatcgg ccaacgcgcg gggagaggcg gtttgcgtat   4680
tgggcgctct tccgcttcct cgctcactga ctcgctgcgc tcggtcgttc ggctgcggcg   4740
agcggtatca gctcactcaa aggcggtaat acggttatcc acagaatcag gggataacgc   4800
aggaaagaac atgtgagcaa aaggccagca aaaggccagg aaccgtaaaa aggccgcgtt   4860
gctggcgttt ttccataggc tccgcccccc tgacgagcat cacaaaaatc gacgctcaag   4920
tcagaggtgg cgaaacccga caggactata aagataccag gcgtttcccc ctggaagctc   4980
cctcgtgcgc tctcctgttc cgaccctgcc gcttaccgga tacctgtccg cctttctccc   5040
ttcgggaagc gtggcgcttt ctcatagctc acgctgtagg tatctcagtt cggtgtaggt   5100
cgttcgctcc aagctgggct gtgtgcacga accccccgtt cagcccgacc gctgcgcctt   5160
atccggtaac tatcgtcttg agtccaaccc ggtaagacac gacttatcgc cactggcagc   5220
agccactggt aacaggatta gcagagcgag gtatgtaggc ggtgctacag agttcttgaa   5280
gtggtggcct aactacggct acactagaag gacagtattt ggtatctgcg ctctgctgaa   5340
gccagttacc ttcggaaaaa gagttggtag ctcttgatcc ggcaaacaaa ccaccgctgg   5400
tagcggtggt ttttttgttt gcaagcagca gattacgcgc agaaaaaaag gatctcaaga   5460
agatcctttg atcttttcta cggggtctga cgctcagtgg aacgaaaact cacgttaagg   5520
gattttggtc atgagattat caaaaaggat cttcacctag atcctttaa attaaaaatg   5580
```

-continued

```
aagttttaaa tcaatctaaa gtatatatga gtaaacttgg tctgacagtt accaatgctt    5640
aatcagtgag gcacctatct cagcgatctg tctatttcgt tcatccatag ttgcctgact    5700
ccccgtcgtg tagataacta cgatacggga gggcttacca tctggcccca gtgctgcaat    5760
gataccgcga gacccacgct caccggctcc agatttatca gcaataaacc agccagccgg    5820
aagggccgag cgcagaagtg gtcctgcaac tttatccgcc tccatccagt ctattaattg    5880
ttgccgggaa gctagagtaa gtagttcgcc agttaatagt ttgcgcaacg ttgttgccat    5940
tgctacaggc atcgtggtgt cacgctcgtc gtttggtatg gcttcattca gctccggttc    6000
ccaacgatca aggcgagtta catgatcccc catgttgtgc aaaaaagcgg ttagctcctt    6060
cggtcctccg atcgttgtca gaagtaagtt ggccgcagtg ttatcactca tggttatggc    6120
agcactgcat aattctctta ctgtcatgcc atccgtaaga tgcttttctg tgactggtga    6180
gtactcaacc aagtcattct gagaatagtg tatgcggcga ccgagttgct cttgcccggc    6240
gtcaatacgg gataataccg cgccacatag cagaacttta aaagtgctca tcattggaaa    6300
acgttcttcg gggcgaaaac tctcaaggat cttaccgctg ttgagatcca gttcgatgta    6360
acccactcgt gcacccaact gatcttcagc atcttttact ttcaccagcg tttctgggtg    6420
agcaaaaaca ggaaggcaaa atgccgcaaa aaagggaata agggcgacac ggaaatgttg    6480
aatactcata ctcttccttt ttcaatatta ttgaagcatt tatcagggtt attgtctcat    6540
gagcggatac atatttgaat gtatttagaa aaataaacaa ataggggttc cgcgcacatt    6600
tccccgaaaa gtgccacctg acgtc                                         6625
```

<210> SEQ ID NO 3
<211> LENGTH: 30
<212> TYPE: DNA
<213> ORGANISM: Artificial sequence
<220> FEATURE:
<223> OTHER INFORMATION: Synthetic sequence of PCR primer for sdpl gene fragment

<400> SEQUENCE: 3

```
tataggcgcc atggatataa gtaatgaggc                                      30
```

<210> SEQ ID NO 4
<211> LENGTH: 30
<212> TYPE: DNA
<213> ORGANISM: Artificial sequence
<220> FEATURE:
<223> OTHER INFORMATION: Synthetic sequence of PCR primer for sdpl gene fragment

<400> SEQUENCE: 4

```
tgtcctgcag ctaagcatct ataacactac                                      30
```

<210> SEQ ID NO 5
<211> LENGTH: 2478
<212> TYPE: DNA
<213> ORGANISM: Arabidopsis thaliana col.

<400> SEQUENCE: 5

```
atggatataa gtaatgaggc tagtgtcgat ccctttccga ttggaccatc atctatcatg      60
ggtcgaacca ttgctttcag agtcttgttc tgtagatcaa tgtcacagct taggcgtgat     120
ctctttcggt tcttgttgca ttggtttctt agatttaagc tgaccgtttc accgtttgtg     180
tcgtggtttc atcctcggaa ccctcaaggg attttagcgg tggttacaat cattgccttt     240
gtgttgaaac gatacacgaa tgtgaaaata aaggcggaaa tggcttaccg gaggaagttt     300
```

```
tggaggaata tgatgcggac ggctttgact tatgaggaat gggctcatgc tgctaagatg    360
ttagagaagg aaacaccaaa gatgaatgaa tctgatcttt atgatgaaga gttggttaag    420
aacaagcttc aggagcttcg tcatcgtcgc caagaaggct cacttagaga cattatgttt    480
tgtatgagag ctgatttggt gaggaatctc ggtaatatgt gtaattcgga gcttcataaa    540
ggtagacttc aggttcctag acatatcaaa gagtacattg atgaggtgtc tactcagttg    600
agaatggttt gtaactctga ttcagaggag ctttctttag aagagaagct ttcttttatg    660
catgaaacac ggcatgcctt tggtagaacg gctttgcttt tgagtggtgg ggcttctctt    720
ggtgcgtttc atgttggtgt ggttaggact ttggttgagc ataagctttt acctcgaata    780
attgctggtt ctagtgttgg atccatcatt tgtgctgttg tggcctcaag gtcttggcca    840
gaactacaga gtttctttga gaattctttg cattctttac agttctttga tcagctcgga    900
ggcgtgttct caatagtgaa acgggtaatg acacaagggg ctctacacga tatcagacag    960
ttgcaatgta tgcttagaaa cctcacaagc aatctcacat ccaagaagc ttatgacatg     1020 acaggaagga ttctcgggat caccgtttgc tccccaagaa agcatgaacc tcctcggtgt    1080
cttaactatt tgacttcgcc tcatgtggtt atatggagcg cagtgactgc ttcttgtgct    1140
tttcctggtc tctttgaagc tcaagagcta atggctaaag atcgaagtgg agagatcgta    1200
ccgtatcatc cacctttcaa tttgatccca gaagtaggca ctaaatcatc atctggacgc    1260
cggtggagag atggtagttt ggaggttgat ttaccaatga tgcagcttaa agaactgttc    1320
aatgtcaatc attttattgt gagccaagcc aatcctcaca ttgctccatt actgcgtcta    1380
aaggatttag ttcgagctta tggtggtaga ttcgcagcta agctcgcgca tctagtggag    1440
atggaggtca aacatagatg caaccaggta ttagagctcg gttttcctct cggtggactc    1500
gcaaagcttt tgctcagga gtgggaaggt gatgttacag ttgtaatgcc tgctactctt     1560
gctcagtact cgaagattat acaaaatccg actcatgtcg agcttcagaa agcggctaac    1620
caaggaagaa gatgcacttg ggagaagctc tcagccataa aatcaaactg cgggatcgag    1680
cttgcgcttg atgattctgt agctattctt aaccatatgc ggaggctcaa gaaaagtgcg    1740
gagagagccg ccactgccac gtcttcgtct catcacggat tggcttcaac caccagattc    1800
aatgcttcaa gaagaatccc atcttggaac gtccttgcca gagagaactc aacaggctca    1860
ctggatgatc tagtcactga caataacctc cacgcttctt cgggcaggaa tttaagcgac    1920
agtgaaacag agagcgtgga gttgagttct tggacaagaa ctggtggacc tttaatgaga    1980
acagcttctg ctaataagtt cattgatttt gttcagagtc ttgatatcga cattgcattg    2040
gtcagaggat ttagtagcag tcccaattct ccagcagttc ctcctggtgg ctcgtttact    2100
ccaagcccga gatccatagc ggctcattcg gatatcgaat caaacagcaa tagcaacaat    2160
cttggaacaa gcacttcaag cataacagtt actgaaggtg atcttctaca gcctgagaga    2220
acgagtaacg gatttgtgtt aaacgtcgtt aaaagagaga acttgggaat gccatcgatt    2280
gggaaccaaa atacagagtt accagagagt gtacagctcg atataccgga aaggagatg     2340 gattgtagct ctgtatcaga acacgaagaa gatgataacg acaatgaaga agaacataac    2400
ggctcgagtc tggttactgt ttcttcagaa gattccggtt tacaagaacc ggtgtctggt    2460
agtgttatag atgcttag                                                  2478
```

<210> SEQ ID NO 6
<211> LENGTH: 57
<212> TYPE: DNA

<213> ORGANISM: Artificial sequence
<220> FEATURE:
<223> OTHER INFORMATION: Synthetic sequence of PCR primer for MSMEG_0220 gene fragment

<400> SEQUENCE: 6
tatatctaga acaacgggga ggacaaccga atggtgagca gcacccgcag tgaacac      57

<210> SEQ ID NO 7
<211> LENGTH: 35
<212> TYPE: DNA
<213> ORGANISM: Artificial sequence
<220> FEATURE:
<223> OTHER INFORMATION: Synthetic sequence of PCR primer for MSMEG_0220 gene fragment

<400> SEQUENCE: 7
tatatctaga tcacagatga ctcacgatcc atgag      35

<210> SEQ ID NO 8
<211> LENGTH: 843
<212> TYPE: DNA
<213> ORGANISM: Mycobacterium smegmatis

<400> SEQUENCE: 8
atggtgagca gcacccgcag tgaacacagc tttgccggcg tcggcggcgt ccgcatcgtc      60
tacgacgtgt ggaccccga caccgacccg cgcggggtcg tcgtgctggc gcacggttac     120
gccgaacacg caggccgcta ccaccacgtc gcgcaacggt tcggggccgc gggcctgctc     180
gtgtacgcac tcgaccaccg cggacacggc cgctccggcg gtaagcgcgt tcacctgcgc     240
gacctgtcgg agttcgtcga ggacttccgc acactcgtcg gcatcgccgc gaacgaccac     300
cccacactgc cgcggatcgt gctcggccac agcatgggcg gcggcatcgt cttcgcctat     360
ggcgctcggt acccgggcga gtactcggcc atggtgctgt ccgggcccgc cgtgaacgca     420
cacgacggcg tatcgccggt gctggtcgcg gtggccaaag tgctgggcaa actcgcgccc     480
ggcatcccgg tggagaacct ggacgccgac gcggtctcgc gcgaccccga ggtggtcgcg     540
gcctacaagg ccgatccgat ggttcaccac ggcaagctgc ccgcgggcat cgcgcgcgcg     600
ctgatcggcc tgggacagag catgccgcag cgggccgcgg cgctgaccgc gccgctgctg     660
gtggtgcacg gcgacaagga ccgcctcatc ccggtggcgg gcagccggct gctcgtcgac     720
cgcgtggctt ccgaggatgt ccacctgaag gtctaccccg ggctgtacca cgaggtgttc     780
aacgaacccg aacagaaact cgtcctcgac gacgtcacct catggatcgt gagtcatctg     840
tga     843

<210> SEQ ID NO 9
<211> LENGTH: 42
<212> TYPE: DNA
<213> ORGANISM: Artificial sequence
<220> FEATURE:
<223> OTHER INFORMATION: Synthetic sequence of ARAT_f primer

<400> SEQUENCE: 9
tatattccat ggggaggaca acatataagt aatgaggcta gt      42

<210> SEQ ID NO 10
<211> LENGTH: 30
<212> TYPE: DNA
<213> ORGANISM: Artificial sequence
<220> FEATURE:
<223> OTHER INFORMATION: Synthetic sequence of ARAT-r primer

<400> SEQUENCE: 10
ccgcctgcag ctaagcatct ataacactac                                    30

<210> SEQ ID NO 11
<211> LENGTH: 51
<212> TYPE: DNA
<213> ORGANISM: Artificial sequence
<220> FEATURE:
<223> OTHER INFORMATION: Synthetic sequence of ATAG7_f primier

<400> SEQUENCE: 11
tattgacgtc gacaacgggg aggacaaccg aatggaacgc ggatccactt g            51

<210> SEQ ID NO 12
<211> LENGTH: 38
<212> TYPE: DNA
<213> ORGANISM: Artificial sequence
<220> FEATURE:
<223> OTHER INFORMATION: Synthetic sequence of ATAG7-r primer

<400> SEQUENCE: 12
cttgtactaa gtcccgggtt agtggacgac ctcgaagc                           38

<210> SEQ ID NO 13
<211> LENGTH: 55
<212> TYPE: DNA
<213> ORGANISM: Artificial sequence
<220> FEATURE:
<223> OTHER INFORMATION: Synthetic sequence of Mlip2_f primer

<400> SEQUENCE: 13
tattggcgcc gacaacgggg aggacaaccg aatggtgagc agcacccgca gtgaa        55

<210> SEQ ID NO 14
<211> LENGTH: 51
<212> TYPE: DNA
<213> ORGANISM: Artificial sequence
<220> FEATURE:
<223> OTHER INFORMATION: Synthetic sequence of Mlip2_r primer

<400> SEQUENCE: 14
ccacgatgga cacgttgtac taagtctgca gtcacagatg actcacgatc c            51

<210> SEQ ID NO 15
<211> LENGTH: 34
<212> TYPE: DNA
<213> ORGANISM: Artificial sequence
<220> FEATURE:
<223> OTHER INFORMATION: Synthetic sequence of PAO_f primer

<400> SEQUENCE: 15
tatagacgtc atgaagaaga agtctctgct cccc                               34

<210> SEQ ID NO 16
<211> LENGTH: 30
<212> TYPE: DNA
<213> ORGANISM: Artificial sequence
<220> FEATURE:
<223> OTHER INFORMATION: Synthetic sequence of PAO_r primer

<400> SEQUENCE: 16
tcgaaagctt ctacaggctg gcgttcttca                                    30

<210> SEQ ID NO 17

<211> LENGTH: 2478
<212> TYPE: DNA
<213> ORGANISM: Arabidopsis thaliana

<400> SEQUENCE: 17

| | | | | | |
|---|---|---|---|---|---|
| atggatataa | gtaatgaggc | tagtgtcgat | cccttttcga | ttggaccatc | atctatcatg | 60 |
| ggtcgaacca | ttgctttcag | agtcttgttc | tgtagatcaa | tgtcacagct | taggcgtgat | 120 |
| ctctttcggt | tcttgttgca | ttggtttctt | agatttaagc | tgaccgtttc | accgtttgtg | 180 |
| tcgtggtttc | atcctcggaa | ccctcaaggg | attttagcgg | tggttacaat | cattgccttt | 240 |
| gtgttgaaac | gatacacgaa | tgtgaaaata | aaggcggaaa | tggcttaccg | gaggaagttt | 300 |
| tggaggaata | tgatgcggac | ggctttgact | tatgaggaat | gggctcatgc | tgctaagatg | 360 |
| ttagagaagg | aaacaccaaa | gatgaatgaa | tctgatcttt | atgatgaaga | gttggttaag | 420 |
| aacaagcttc | aggagcttcg | tcatcgtcgc | caagaaggct | cacttagaga | cattatgttt | 480 |
| tgtatgagag | ctgatttggt | gaggaatctc | ggtaatatgt | gtaattcgga | gcttcataaa | 540 |
| ggtagacttc | aggttcctag | acatatcaaa | gagtacattg | atgaggtgtc | tactcagttg | 600 |
| agaatggttt | gtaactctga | ttcagaggag | ctttctttag | aagagaagct | ttctttatg | 660 |
| catgaaacac | ggcatgcctt | tggtagaacg | gctttgcttt | tgagtggtgg | ggcttctctt | 720 |
| ggtgcgtttc | atgttggtgt | ggttaggact | ttggttgagc | ataagctttt | acctcgaata | 780 |
| attgctggtt | ctagtgttgg | atccatcatt | tgtgctgttg | tggcctcaag | gtcttggcca | 840 |
| gaactacaga | gtttctttga | gaattctttg | cattctttac | agttctttga | tcagctcgga | 900 |
| ggcgtgttct | caatagtgaa | acgggtaatg | acacaagggg | ctctacacga | tatcagacag | 960 |
| ttgcaatgta | tgcttagaaa | cctcacaagc | aatctcacat | tccaagaagc | ttatgacatg | 1020 |
| acaggaagga | ttctcgggat | caccgtttgc | tccccaagaa | agcatgaacc | tcctcggtgt | 1080 |
| cttaactatt | tgacttcgcc | tcatgtggtt | atatggagcg | cagtgactgc | ttcttgtgct | 1140 |
| tttcctggtc | tctttgaagc | tcaagagcta | atggctaaag | atcgaagtgg | agagatcgta | 1200 |
| ccgtatcatc | cacctttcaa | tttggatcca | gaagtaggca | ctaaatcatc | atctggacgc | 1260 |
| cggtggagag | atggtagttt | ggaggttgat | ttaccaatga | tgcagcttaa | agaactgttc | 1320 |
| aatgtcaatc | attttattgt | gagccaagcc | aatcctcaca | ttgctccatt | actgcgtcta | 1380 |
| aaggatttag | ttcgagctta | tggtggtaga | ttcgcagcta | agctcgcgca | tctagtggag | 1440 |
| atggaggtca | acatagatg | caaccaggta | ttagagctcg | gttttcctct | cggtggactc | 1500 |
| gcaaagcttt | tgctcagga | gtgggaaggt | gatgttacag | ttgtaatgcc | tgctactctt | 1560 |
| gctcagtact | cgaagattat | acaaaatccg | actcatgtcg | agcttcagaa | agcggctaac | 1620 |
| caaggaagaa | gatgcacttg | ggagaagctc | tcagccataa | aatcaaactg | cgggatcgag | 1680 |
| cttgcgcttg | atgattctgt | agctattctt | aaccatatgc | ggaggctcaa | gaaaagtgcg | 1740 |
| gagagagccg | ccactgccac | gtcttcgtct | catcacggat | tggcttcaac | caccagattc | 1800 |
| aatgcttcaa | gaagaatccc | atcttggaac | gtccttgcca | gagagaactc | aacaggctca | 1860 |
| ctggatgatc | tagtcactga | caataacctc | cacgcttctt | cgggcaggaa | tttaagcgac | 1920 |
| agtgaaacag | agagcgtgga | gttgagttct | tggacaagaa | ctggtggacc | tttaatgaga | 1980 |
| acagcttctg | ctaataagtt | cattgatttt | gttcagagtc | ttgatatcga | cattgcattg | 2040 |
| gtcagaggat | ttagtagcag | tcccaattct | ccagcagttc | ctcctggtgg | ctcgtttact | 2100 |
| ccaagcccga | gatccatagc | ggctcattcg | gatatcgaat | caaacagcaa | tagcaacaat | 2160 |
| cttggaacaa | gcacttcaag | cataacagtt | actgaaggtg | atcttctaca | gcctgagaga | 2220 |

```
acgagtaacg gatttgtgtt aaacgtcgtt aaaagagaga acttgggaat gccatcgatt    2280
gggaaccaaa atacagagtt accagagagt gtacagctcg atataccgga gaaggagatg    2340
gattgtagct ctgtatcaga acacgaagaa gatgataacg acaatgaaga agaacataac    2400
ggctcgagtc tggttactgt ttcttcagaa gattccggtt tacaagaacc ggtgtctggt    2460
agtgttatag atgcttag                                                  2478
```

<210> SEQ ID NO 18
<211> LENGTH: 1047
<212> TYPE: DNA
<213> ORGANISM: Aspergillus fumigatus

<400> SEQUENCE: 18

```
atggaacgcg gatccacttg cgtcataagg actgcggctt ctcgatcaca atggacgact     60
atggtacatg ttggtgcaga attgaatgcg tctgcacaag taaggtttct tcgcagcctg    120
tgtaggtttc gatcatttag ttcttcctat cggagcttcc acgctttgcc gtgcaggagc    180
aaatcacata agcatatagg ttccgatgct cttgaccctc gccttgatga tcttggaaag    240
gtcttacgag acgaatatgc ggtgatccga gatcattacg aaaccccaaa gtatccagtt    300
gtccttgcgc atgggctcct aggttttgat gagttacgcc tcgctggccc tctccttcct    360
ggagttcagt actggcgagg aatcaaggaa gctttgaccc agaaaggagt gcaagtcatc    420
actgcaacag tacctccttc ggggtccatt gagatgcgtg cggaggagct ggtgaaggat    480
atagatgagg gcgcccaggg gaaagctgta aatattattg cgggccttga tgctcgttac    540
atgataagtc gtctaagacc gaagaagttc aaggtcttgt ctttgacgac aattgcgact    600
cctcatcgtg gttctacggt tgcagattat gtccttgagc gaattggtga cgagcggcta    660
ccccagttat attacactct cggaaaactc aaggttgaaa ctggagcctt tcccagttg     720 acgcgcaagt atatggaaga tacgttcaat ccagccacgc ctgacgttga ggatgttcgt    780
tacttcagct acggcgcagc gatgcaacca agcttttggt ctatgttccg cttgtcccat    840
cgcgttcttc aagaggtgga aggatataac gatgggctag tcagcgtcgc tagcagcaaa    900
tggggaaaat acaaaggcac cctggaaggg gccagccacc tggatttgat caactggacc    960
aacaggctga gtggcttgc gggcgagata actggaaaca ggcaaaggtt tgtaaaatct   1020
atctctggct tcgaggtcgt ccactaa                                      1047
```

<210> SEQ ID NO 19
<211> LENGTH: 936
<212> TYPE: DNA
<213> ORGANISM: Pseudomonas aeruginosa

<400> SEQUENCE: 19

```
atgaagaaga agtctctgct ccccctcggc ctggccatcg tctcgcctc tctcgctgcc      60 agccctctga tccaggccag cacctacacc cagaccaaat accccatcgt gctggcccac    120
ggcatgctcg gcttcgacaa catcctcggg gtcgactact ggttcggcat tcccagcgcc    180
ttgcgccgtg acggtgccca ggtctacgtc accgaagtca gccagttgga cacctcggaa    240
gtccgcggcg agcagttgct gcaacaggtg gaggaaatcg tcgccctcag cggccagccc    300
aaggtcaacc tgatcggcca cagccacggc gggccgacca tccgctacgt cgccgccgta    360
cgtcccgacc tgatcgcttc cgccaccagc gtcggcgccc cgcacaaggg ttcggacacc    420
gccgacttcc tgcgccagat cccaccgggt tcggccggcg aggcagtcct ctccgggctg    480
```

```
gtcaacagcc tcggcgcgct gatcagcttc ctttccagcg gcagcaccgg tacgcagaat    540
tcactgggct cgctggagtc gctgaacagc gagggtgccg cgcgcttcaa cgccaagtac    600
ccgcagggca tccccacctc ggcctgcggc gaaggcgcct acaaggtcaa cggcgtgagc    660
tattactcct ggagcggttc ctcgccgctg accaacttcc tcgatccgag cgacgccttc    720
ctcggcgcct cgtcgctgac cttcaagaac ggcaccgcca acgacggcct ggtcggcacc    780
tgcagttcgc acctgggcat ggtgatccgc gacaactacc ggatgaacca cctggacgag    840
gtgaaccagg tcttcggcct caccagcctg ttcgagacca gcccggtcag cgtctaccgc    900
cagcacgcca accgcctgaa gaacgccagc ctgtag                              936

<210> SEQ ID NO 20
<211> LENGTH: 936
<212> TYPE: DNA
<213> ORGANISM: Mycobacterium smegmatis

<400> SEQUENCE: 20
atgaagaaga agtctctgct cccctcggc ctggccatcg gtctcgcctc tctcgctgcc      60
agccctctga tccaggccag cacctacacc cagaccaaat acccatcgt gctggcccac     120 ggcatgctcg gcttcgacaa catcctcggg gtcgactact ggttcggcat tcccagcgcc    180
ttgcgccgtg acggtgccca ggtctacgtc accgaagtca gccagttgga cacctcggaa    240
gtccgcggcg agcagttgct gcaacaggtg gaggaaatcg tcgccctcag cggccagccc    300
aaggtcaacc tgatcggcca cagccacggc gggccgacca tccgctacgt cgccgccgta    360
cgtcccgacc tgatcgcttc cgccaccagc gtcggcgccc cgcacaaggg ttcggacacc    420
gccgacttcc tgcgccagat cccaccgggt tcggccggcg aggcagtcct ctccgggctg    480
gtcaacagcc tcggcgcgct gatcagcttc ctttccagcg gcagcaccgg tacgcagaat    540
tcactgggct cgctggagtc gctgaacagc gagggtgccg cgcgcttcaa cgccaagtac    600
ccgcagggca tccccacctc ggcctgcggc gaaggcgcct acaaggtcaa cggcgtgagc    660
tattactcct ggagcggttc ctcgccgctg accaacttcc tcgatccgag cgacgccttc    720
ctcggcgcct cgtcgctgac cttcaagaac ggcaccgcca acgacggcct ggtcggcacc    780
tgcagttcgc acctgggcat ggtgatccgc gacaactacc ggatgaacca cctggacgag    840
gtgaaccagg tcttcggcct caccagcctg ttcgagacca gcccggtcag cgtctaccgc    900
cagcacgcca accgcctgaa gaacgccagc ctgtag                              936
```